United States Patent [19]

Schraga

[11] Patent Number: 5,518,004
[45] Date of Patent: May 21, 1996

[54] SPECIMEN DRAWING DEVICE

[76] Inventor: Steven Schraga, 1841 NE. 146 St., North Miami, Fla. 33181

[21] Appl. No.: 353,910

[22] Filed: Dec. 12, 1994

[51] Int. Cl.$^6$ ........................................ A61B 5/00
[52] U.S. Cl. .................. 128/763; 604/187; 604/240
[58] Field of Search .................. 604/187, 110, 604/192, 198, 263, 240, 242, 243; 128/763, 764, 765

[56] References Cited

U.S. PATENT DOCUMENTS

| | | | |
|---|---|---|---|
| 4,841,985 | 6/1989 | Wanamaker | 128/763 |
| 4,907,600 | 3/1990 | Spencer | 604/240 X |
| 5,070,885 | 12/1991 | Bonaldo | 128/763 |
| 5,086,780 | 2/1992 | Schmitt | 128/763 |
| 5,201,716 | 4/1993 | Richard | 604/187 |

*Primary Examiner*—John D. Yasko
*Attorney, Agent, or Firm*—Malloy & Malloy

[57] ABSTRACT

An improved specimen drawing device to be used to safely and cost effectively draw specimens such as blood from a patient, the device including a reusable main tubular housing, with a side wall structure defining an open proximal end, an at least partially open distal end and an open interior, and a disposable cannula assembly, having an elongate cannula and a protective shield disposed in surrounding relation about a central portion of the elongate cannula so as to maintain the elongate cannula axially disposed in spaced relation from the reusable tubular housing, the protective shield being structured for removable, yet secured engagement with the distal end of the tubular housing so as to allow for disposability of the entire cannula assembly. The protective shield being removably secured to the tubular housing and being structured for facilitated and remote disengagement thereof from the tubular housing so as to maintain a user's fingers in remote spaced apart relation from the elongate cannula and to ensure that portions of the disposable cannula assembly which come into contact with the specimen will not come into contact with a user or portions of the reusable main tubular housing.

14 Claims, 1 Drawing Sheet

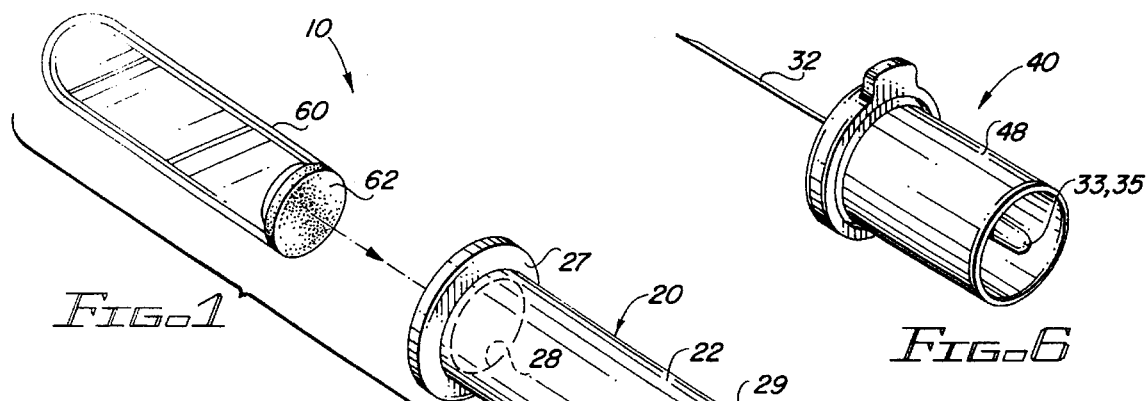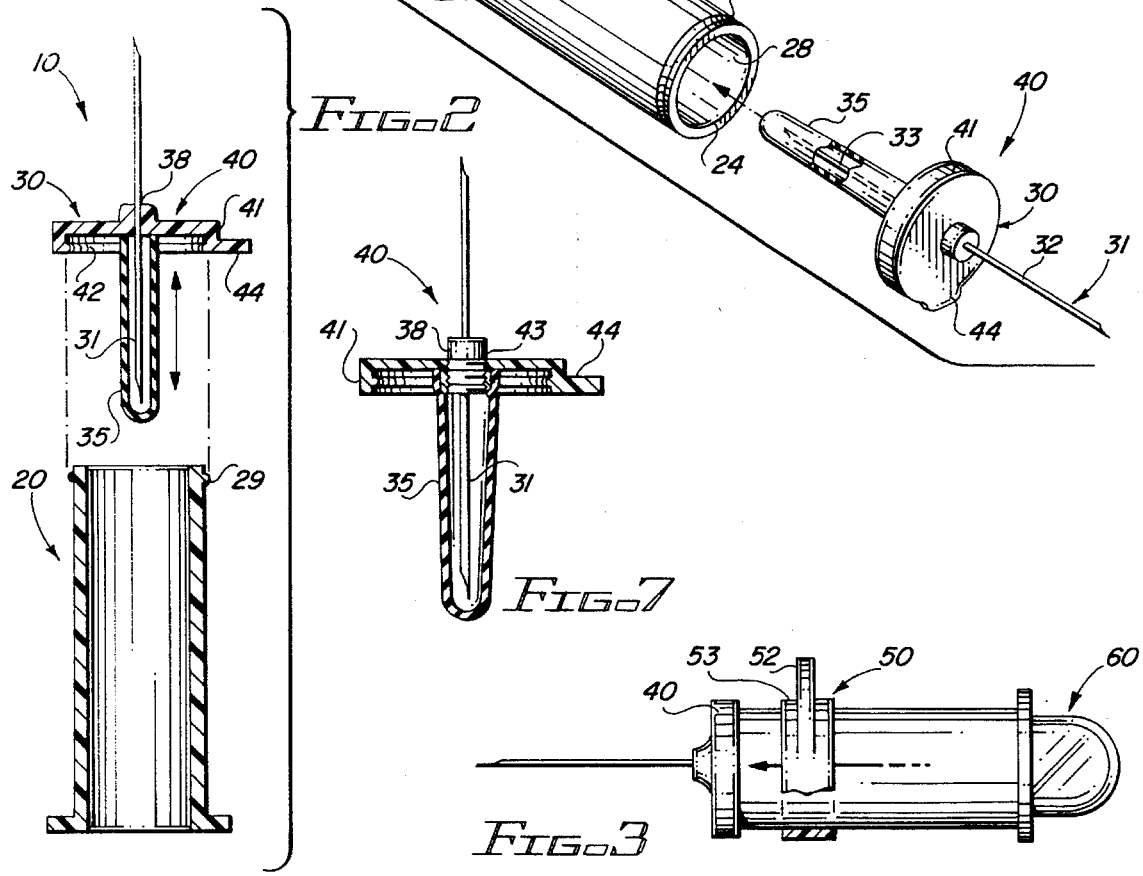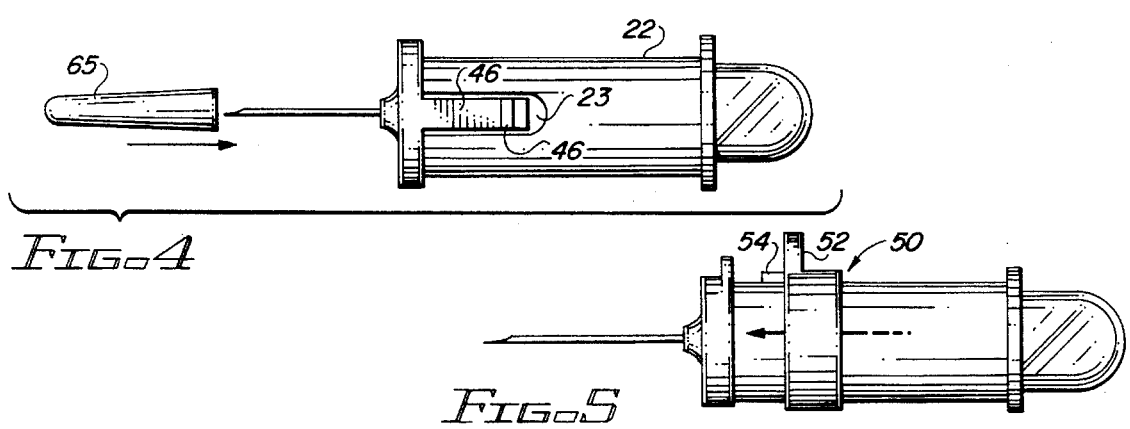

SPECIMEN DRAWING DEVICE

BACKGROUND OF THE INVENTION

1. Field of the Invention

The present invention relates to an improved specimen drawing device structured to facilitate the rapid drawing of a blood specimen from a patient in a cost effective, highly sanitary, and safe manner.

2. Description of the Related Art

One of the most common medical procedures performed on a patient involves the drawing of a blood specimen. Generally, one or a plurality of test tubes of blood are drawn for the purpose of testing and experimentation. Due to the amount of blood needed and further due to the various and numerous testing which must be performed on the blood specimens, conventional, disposable syringes cannot be practically utilized. Further, because of the frequent rate at which blood samples are taken, it can become quite expensive if an entire, disposable syringe must be utilized for each tube of blood to be drawn.

For these reasons, the art has turned to partially disposable specimen drawing devices. These partially disposable devices will generally include a reusable housing into which a sample collection apparatus, such as a test tube, will be interchangeably inserted. Further, because of the costs involved and frequent use of the device, the needle/cannula portion will generally be the sole disposable part of the entire apparatus, thereby enabling reuse of the housing by replacement of a new needle/cannula.

In the art, the most common type of blood drawing devices includes a hollow tubular housing wherein a disposable needle assembly is secured. In use, a portion of the needle will extend into the interior of the housing and an exterior portion of the needle, will extend out from the housing. When ready to use, the interior portion of the needle will be connected with a test tube or like collecting device, and the exterior portion will be inserted into a patient for drawing of the blood specimen. Once the sample is drawn, however, potentially hazardous circumstances arise.

Specifically, once a hospital worker has finished taking a blood sample, he or she must dispose of the needle portion. Generally, this will require replacing a protective cap or sheath over the needle tip, unscrewing the needle, and properly disposing of the needle in an approved waste container. Alternatively, some hospital workers will merely unscrew the needle without recapping, or will insert the needle portion into a sharp box rather than the cap before unscrewing the housing and disposing of the needle assembly. Such procedures, however, have many hazards involved therewith. For example, a primary hazard to health care workers involves replacement of the protective sheath, which should be a preliminary step to the unscrewing of the needle assembly. Because of the often stressful or rushed circumstances involved, it is a common occurrence during replacement that an interior of the sheath will be missed by the needle and the health care worker will be pricked by the needle tip. Additionally, there is a problem with blood contaminating the reusable portions of the apparatus. Generally, most disposable needles will include a retractable rubber guard over a portion of the needle that extends into the housing. The retractable guard will retract when the needle assembly is coupled with the test tube, and when the test tube is pulled from the needle the retractable guard extends back over the needle into its protective covering orientation. However, as this closure is taking place, the guard acts as a wipe which wipes blood from the external perimeter surface of the needle portion being covered. Consequently, a quantity of blood can remain at a tip of the retractable guard which can contact and contaminate the housing when the needle is unscrewed. Further, the blood can also run down an exterior surface of the retractable guard resulting in contamination of the surrounding reusable housing.

Accordingly, there is a substantial need in the art for a specimen drawing device which provides maximum safety and easy disposal of blood contacting portions, and which will appropriately isolate the blood contacting portions from reusable parts of the device.

In the past, others have attempted to address the disposability of the needle assembly, through the use of hinged or spring biased pivots to assist with ejecting the needle after use. While these devices eliminate the need to specifically unscrew the needle from the housing, they can also be quite expensive due to the number of moving parts and intricate interconnections which can lead to expensive molding and labor intensive manufacturing. Further, such devices do not address the important problem of contamination of the reusable portions of the assembly when attempting to dispose of the needle alone.

Therefore, there is still a need for a product which maximizes the overall safety involved in disposal and reuse of a select portion of the assembly, while maintaining the ease of use and low expense necessary to provide an effective and readily usable specimen drawing assembly.

SUMMARY OF THE INVENTION

The present invention is directed to an improved specimen drawing device, which will preferably be utilized to draw blood specimens from a patient. Specifically, the specimen drawing device will include a reusable main tubular housing, a disposable cannula assembly, and sample collection means.

The reusable main tubular housing of the device will include a side wall structure which defines an open proximal end, an at least partially open distal end, and an open interior. Structured to be coupled with the tubular housing is the disposable cannula assembly. The disposable cannula assembly includes an elongate cannula with a piercing end and a coupling end, the piercing end being structured for insertion into a patient. Disposed in surrounding relation about a central portion of the elongate cannula, between the piercing end and the coupling end, is a protective shield. This protective shield is specifically structured for removable engagement with the tubular housing, at the distal end of the tubular housing, such that the coupling end of the elongate cannula will extend into the open interior of the tubular housing and the piercing end will extend out from the tubular housing. Further, the protective shield will secure the cannula assembly to the tubular housing in such a manner that the elongate cannula will be axially disposed in a substantially spaced apart relation from the tubular housing, thereby protecting the tubular housing from any direct or close contact with the coupling end of the elongate cannula both before and after blood is drawn. As additional safety, the coupling end will include an independent, retractable guard which functions to shield the coupling end before and after blood is drawn.

Also included as part of the device are release means. The release means will be disposed in remote spaced apart relation from the elongate cannula and are structured to disengage the protective shield from its secure engagement with the housing when disposal of the cannula assembly is desired. Accordingly, a user's fingers need not come into close contact with the used cannula.

Regarding the sample collection means, it will preferably have a vacuum formed therein and be structured to be at least partially inserted into the open interior of the tubular housing, through its proximal end, for coupled engagement with the coupling end of the elongate cannula. By securing its coupled engagement with the cannula, extraction of the sample through the elongate cannula and directly into a collection container containing the vacuum is facilitated.

It is an object of the present invention to provide a specimen drawing device which is easy and cost effective to manufacture and utilize.

Still another object of the present invention is to provide a specimen drawing device which requires no contact between a sample taker and the cannula/needle portions both during assembly and disposal of the cannula assembly of the device.

Yet another object of the present invention is to provide a specimen drawing device which will isolate the cannula assembly and in particular the coupling end and retractable guard which come into contact with a patient's blood, from the reusable portion of the device, thereby preventing possible contamination of the reusable portion or the sample taker.

An additional object of the present invention is to provide a specimen drawing device which is easy to assemble for immediate use.

Another object of the present invention is to provide a specimen drawing device which is easy and safe to disassemble for immediate disposal and without direct contact by a sample taker.

Still another object of the present invention is to provide a specimen drawing device which is capable of adaptation for use with existing disposable needles.

BRIEF DESCRIPTION OF THE DRAWINGS

For a fuller understanding of the nature of the present invention, reference should be had to the following detailed description taken in connection with the accompanying drawings in which:

FIG. 1 is a perspective, exploded view of an embodiment of the specimen drawing device of the present invention.

FIG. 2 is a cross-sectional, partially exploded view of the specimen drawing device of the present invention.

FIG. 3 is a side view of an alternative embodiment of the specimen drawing device of the present invention.

FIG. 4 is a side view of an additional alternative embodiment of the specimen drawing device of the present invention.

FIG. 5 is yet another side view of an alternative embodiment of the specimen drawing device of the present invention.

FIG. 6 is an isolated perspective view of an alternative embodiment of the disposable cannula assembly of the present invention.

FIG. 7 is a cross-sectional, partially exploded view of another embodiment of the specimen drawing device of the present invention.

Like reference numerals refer to like parts throughout the several views of the drawings.

DETAILED DESCRIPTION OF THE PREFERRED EMBODIMENT

Shown throughout the figures, the present invention is directed towards a specimen drawing device, generally indicated as 10. The specimen drawing device 10 will preferably be utilized to draw blood samples from a patient for testing purposes, and as such, will include a reusable main tubular housing 20, a disposable cannula assembly 30, and sample collection means 60.

Turning specifically to the main tubular housing 20, it will preferably be formed of an easily moldable, rigid plastic material in order to facilitate multiple repeated uses. Included in the reusable main tubular housing 20 is a side wall structure 22 which defines an open proximal end 26, an at least partially open distal end 24 and an open interior 28. The side wall structure 22 will preferably define a cylindrical configuration and may also include a flanged lip 27, or similar structure conventionally known as "ears", at least partially about the open proximal end 26. The flanged lip 27 is structured to facilitate holding and gripping of the housing 20 and to facilitate insertion of the sample collection means 60 through the open proximal end 26 and into the open interior 28.

Structured to be coupled with the tubular housing 20, at its distal end 24, is the disposable cannula assembly 30. The cannula assembly 30 includes primarily an elongate cannula 31. The cannula 31 has a piercing end 32, a coupling end 33, and an axial channel extending therebetween to allow the flow of the specimen, such as blood, therethrough from the piercing end 32 to the coupling end 33. Specifically, the piercing end 32 is structured to be inserted into a patient from which the specimen will be drawn, while the coupling end 33 is structured for coupled engagement with the sample collection means 60. Disposed on the coupling end 33 will be a retractable guard 35. The retractable guard 35 will preferably include a flexible, resilient material cover, such as rubber, which will be disposed in completely covering relation about the piercing end 33 of the elongate cannula 31. Further, the material cover 35 can include a distal aperture, or alternatively, can be structured to be pierced, such that upon coupling insertion of the coupling end 33 of the elongate cannula 31 with the sample collection means 60, the flexible, resilient material cover 35 will retract exposing the coupling end 33. Similarly, when the coupling end 33 is removed from its coupled engagement with the sample collection means 60, the resilient material cover 35 will return to its relaxed, covering relation about the coupling end 33, thereby achieving maximum safety when not coupled.

Positioned in surrounding relation about a central portion 38 of the elongate cannula 31, between the piercing end 32 and coupling end 33, is a protective shield 40. The protective shield will preferably have a generally rounded configuration to correspond the configuration of the tubular housing 20 and will be structured for removable engagement with the tubular housing 20 at its distal end 24. Preferably, the distal end 24 of the tubular housing 20 will be substantially, if not completely, open, the protective shield 40 being structured to be positioned thereover in covering relation to the distal end 24. Upon engagement of the protective shield 40 with the tubular housing 20, the coupling end 33 of the elongate cannula will extend into the open interior 28 of the tubular housing 20, and the piercing end 32 of the elongate cannula 31 will extend away from the tubular housing 20.

As shown in the drawings, the protective shield 40 is structured such that upon engagement with the tubular housing 20, the elongate cannula 31 will be axially disposed in substantially spaced apart relation from the tubular housing 20. This spaced apart relation between the elongate cannula 31 and the tubular housing 20 will enable the protective shield 40 to shield the tubular housing 20, which is reusable, from drips of the blood specimen which may result when the sample collection means 60 are removed from the coupling end 33 of the elongate cannula 31. Specifically, an unaddressed, and often unrecognized problem associated with the combined use of disposable cannula portions and reusable housing portions involves the susceptibility of blood which collects on an exterior of the retractable guard 35 coming into contact with the reusable housing and/or the sample taker. Specifically, as the retractable guard 35 moves back into a covering position over the coupling end 33, blood or fluid on an exterior of the coupling end is wiped off and accumulated on an exterior of the retractable guard 35. This blood can then come into contact with a conventional housing leading to contamination. In the present invention, any blood or fluid which collects on an exterior of the retractable housing 35 will be prevented from contacting the housing 20 during removal of the cannula assembly 30 due to the spacing between the canula assembly 30 and the housing 20 provided by the protective shield 40. Further, any blood that runs down an exterior of the retractable housing 35 towards the central portion 38 of the elongate cannula 31 will contact the protective shield 40 and will be properly disposed of without contaminating the reusable portion of the device 10. As an additional, alternative safety feature, as illustrated in FIG. 6, a retaining wall 48 can also be included. The wall 48 is structured to extend from the protective shield 40 so as to completely encircle and contain the coupling end 33 of the elongate cannula 31. In this regard, the sample collection means 60 will be inserted within the retaining wall 48 for its coupled engagement with the coupling end 33, but any specimen drips will be completely contained by the protective shield 40.

The protective shield 40 is specifically structured for removable, yet secure engagement with the tubular housing 20. In the preferred embodiment, the protective shield 40 will include a flanged lip 41 disposed at least partially, but preferably completely about a perimeter of the protective shield 40. This flanged lip 41 will be structured to pass over the tubular housing 20, at the distal end 24 thereof, into a snug, yet disengageable connection. In the preferred embodiment, the flanged lip 41 will include an interior rib 42 adapted for mating passage over a corresponding notch or ridge 29 disposed on the tubular housing 20. Accordingly, during coupling engagement, the protective shield will be snapfitted on the housing 20.

Alternatively, the flange lip 41 may be dimensioned such that it will merely slide onto the tubular housing 20 and be snugly engaged therewith due to the corresponding interior diameter of the flange lip 41 and exterior diameter of the tubular housing 20. In a further embodiment illustrated in FIG. 4, at least one elongate flange 46 is included and extends from the protective shield 40. In this embodiment, one or a plurality of the elongate flanges 46 are utilized to maintain the protective shield 40 removably secured to the tubular housing 20 and preferably will embrace an exterior surface of side wall structure 22 of the housing 20. It should be noted, however, that the previously recited structures to provide for removable engagement of the protective shield 40 and tubular housing 20 are merely the preferred methods at the time of invention. It is contemplated that alternative, and equally effective methods for removable engagement may also be effectively utilized, such methods including those methods commonly utilized to secure removable lids to containers.

Also included in the specimen drawing device 10 are release means. The release means can undertake many differing configurations, all structured to disengage the protective shield 40 from its secure engagement with the housing 20, thereby allowing for disposal of the entire cannula assembly 30, without bringing a user's fingers into close relation with the contaminated elongated cannula 31. In the preferred embodiment, the release means will include a tab 44 which protrudes from the protective shield 40. The tab 44 is positioned to allow for effective actuation by a user merely by pushing upon the tab 44, such as with a thumb, until the cannula assembly 30 becomes disengaged from the reusable housing 20 whereupon it can be simultaneously dropped into a disposal container. Alternatively, however, the release means can include a push release member 50. This push release member 50 will preferably be disposed in sliding relation about the tubular housing 20, but can alternatively be only partially disposed about the tubular housing or be built into the tubular housing so long as it provides for slided movement towards the protective shield 40. In a preferred embodiment, the push release member 50 will be structured with a thumb guard 52 to protect a user's finger upon actuation of the push release member 50 and will facilitate pushing of the push release member 50. Specifically, the push release member 50 will preferably be pushed until a contact end 53, as illustrated in FIG. 3, comes into contact with the protective shield 40, pushing the protective shield 40 from its engaged position about the tubular housing 20 and disengaging the cannula assembly 30. Alternatively, the push release member 50 can include a protruding lip 54, seen in FIG. 5, which is structured to engage the tab 44 which extends from the protective shield 40. Contact between the lip 54 and tab 44 will disengage the cannula assembly 30 from the tubular housing 20. As yet another alternative embodiment, illustrated in FIG. 4, the elongate flange 46 can include a raised portion 47 to allow for pushed engagement by a user. This elongate flange 46 can slide within a track 23 formed within the side wall structure 22 of the tubular housing 20, thereby allowing for facilitated sliding disengagement of the cannula assembly 30 from the tubular housing 20. As with the protective shield 40, it is contemplated that a variety of release means may be effectively employed in order to achieve the complete disengagement of the cannula assembly 30 from the tubular housing 20.

Turning to the sample collection means 60, they are structured to be at least partially inserted into the open interior 28 of the tubular housing 20, through the open proximal end 26, for coupled engagement with the coupling end 33 of the elongate cannula 31. Accordingly, extraction of the sample is facilitated through the elongate cannula 31 and into the sample collection means 60 which will include a collection container such as a test tube. Further, the collection container will preferably have a vacuum formed therein such that upon fluid flow engagement with the cannula assembly 30, the specimen is drawn into the collection container. Generally, the sample collection means 60 will be any conventional sample collection means normally utilized with blood sample collection devices. A common variation includes the collection container 60 having a penetrable cover or diaphragm 62 which maintains the vacuum within the container and wherethrough the coupling end 33 is inserted and against which the retractable guard 35 will abut so as to retract during penetration of the coupling end 33 into the sample collection means 60.

In order to allow for facilitated adaptation with existing systems which incorporate disposable needles alone, the protective shield 40 may be structured to include a central opening 43 as shown in FIG. 7, wherein a threaded hub at a central portion 38 of the elongate cannula 31 may be secured. Allowing for secured engagement of a disposable elongate cannula 31 into the protective shield 40, however, will not eliminate the disposable nature of the protective shield 40. It is an important feature of the present invention to ensure that the elongate cannula 31 will be maintained in an axial orientation which is spaced apart from the reusable portion of the overall device 10, and to eliminate the need for user contact with both the piercing end 32 and the coupling end 33 of the cannula 31. When using a conventional, disposable cannula, the cannula 31 can be secured within the disposable protective shield 40 for engagement with the tubular housing 20. After use, complete disposal will include disposal of the entire cannula assembly 30 including the elongate cannula 31 and protective shield 40. For additional safety, a removable sheath 65 shown in FIG. 4, can also be included to cover the piercing end 32 of the elongate cannula 31 prior to use. Similarly, a sheath to cover the coupling end 33 can also be included. Utilizing the device of the present invention, however, it is preferred that disposal of the cannula assembly 30 be achieved through disengagement of the protective shield 40 from the tubular housing 20 and that neither a sheath over the coupling end 33 nor the removable sheath 65 be replaced as it may be hazardous and can lead to pricking or other inadvertent contamination of a user if replacement is attempted.

While this invention has been shown and described in what is considered to be a practical and preferred embodiment, it is recognized that departures may be made within the spirit and scope of this invention which should, therefore, not be limited except as set forth in the claims which follow and within the doctrine of equivalents.

Now that the invention has been described,
What is claimed is:

1. An improved specimen drawing device comprising:
   (a) a re-useable main tubular housing, said main tubular housing including a side wall structure defining an open proximal end, a substantially open open distal end and an open interior,
   (b) a disposable cannula assembly structured to be coupled with said tubular housing at said distal end, said cannula assembly comprising:
      an elongate cannula including a piercing end and a coupling end,
      said coupling end including a retractable guard,
      a protective shield disposed in surrounding relation about a central portion of said elongate cannula between said piercing end and said coupling end,
      said protective shield being structured for completely removable, yet secure engagement with said tubular housing at said distal end thereof so as to substantially define a front distal wall of said tubular housing so that said coupling end of said elongate cannula extends into said open interior of said tubular housing and said elongate cannula is axially disposed in substantially spaced apart relation from said tubular housing,
   (c) release means disposed in remote spaced apart relation from said elongate cannula and structured to disengage said protective shield from said housing for disposal of said cannula assembly, and
   (d) sample collection means structured to be at least partially inserted into said open interior of said tubular housing, through said open proximal end thereof, for coupled engagement with said coupling end of said elongate cannula so as to facilitate extraction of the sample through said elongate cannula and into a collection container.

2. An improved specimen drawing device as recited in claim 1 wherein said retractable guard of said coupling end of said elongate cannula includes a flexible, resilient material cover disposed about said coupling end and including a distal aperture, said resilient material cover being structured to retract upon abutting contact of said distal end of said resilient material cover with said sample collection means during insertion of said coupling end into said sample collection means.

3. An improved specimen drawing device as recited in claim 1 wherein said release means includes a tab protruding from an exterior of said protective shield and structured to facilitate actuation by a user in order to disengage said protective shield from its engagement with said tubular housing.

4. An improved specimen drawing device as recited in claim 3 further including a push release member disposed on said tubular housing and structured to engage said tab extending from said protective shield in order to disengage said protective shield from said tubular housing and to shield a finger of the user which is actuating said push release member.

5. An improved specimen drawing device as recited in claim 1 wherein said protective shield includes a flanged lip disposed at least partially about a perimeter thereof, said flanged lip being structured and disposed for snapped engagement with said tubular housing at said distal end thereof.

6. An improved specimen drawing device as recited in claim 5 wherein said release means includes a tab extending from said flanged lip of said protective shield and structured to facilitate actuation by a user in order to disengage said protective shield from its engagement with said tubular housing.

7. An improved specimen drawing device as recited in claim 6 further including a push release member disposed on said tubular housing and structured to engage said tab extending from said protective shield in order to disengage said protective shield from said tubular housing and to shield a finger of the user which is actuating said push release member.

8. An improved specimen drawing device as recited in claim 1 wherein said cannula assembly includes a removable sheath structured for secured, removable engagement over said piercing end of said elongate cannula.

9. An improved specimen drawing device as recited in claim 1 further including a push release member disposed on said tubular housing and structured to engage said release means of said cannula assemble in order to disengage said protective shield from said tubular housing.

10. An improved specimen drawing device as recited in claim 1 wherein said elongate cannula includes a central hub structured and disposed for secure engagement of said elongate cannula with said protective shield.

11. An improved specimen drawing device as recited in claim 1 wherein said retractable guard of said coupling end of said elongate cannula includes a flexible, resilient material cover disposed about said coupling end and is structured to be pierced by said coupling end of said elongate cannula and to retract upon abutting contact of said distal end of said resilient material cover with said sample collection means during insertion of said coupling end into said sample collection means.

12. An improved specimen drawing device as recited in claim 1 wherein said protective shield includes a retaining wall extending therefrom in surrounding, shielding relation about said coupling end of said elongate cannula and structured to receive said sample collection means therein for coupled engagement with said coupling end of said elongate cannula.

13. An improved specimen drawing device as recited in claim 1 wherein said protective shield includes an elongate flange extending therefrom and is structured and disposed for removable engagement of said cannula assembly with said tubular housing at said distal end thereof.

14. To be coupled to an at least partially open distal end of a re-useable main tubular housing of a specimen drawing device, the re-useable main tubular housing also having a side wall structure defining an open proximal end, the at least partially open distal end and an open interior, a disposable cannula assembly comprising:

an elongate cannula including a piercing end and a coupling end, said coupling end including a retractable guard, a protective shield disposed in surrounding relation about a central portion of said elongate cannula between said piercing end and said coupling end, said protective shield being structured for removable engagement with said housing at said distal end thereof such that said coupling end of said elongate cannula extends into said open interior of said tubular housing and said elongate cannula is axially disposed in substantially spaced apart relation from said side tubular housing, and release means disposed in remote spaced apart relation from said elongate cannula and structured to disengage said protective shield from said housing for disposal of said cannula assembly.

\* \* \* \* \*